US008366762B2

(12) United States Patent
Hossainy et al.

(10) Patent No.: US 8,366,762 B2
(45) Date of Patent: Feb. 5, 2013

(54) METHOD OF MAKING A MEDICAL DEVICE WITH REGIOSELECTIVE STRUCTURE-PROPERTY DISTRIBUTION

(75) Inventors: Syed F. A. Hossainy, Fremont, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 172 days.

(21) Appl. No.: 12/796,543

(22) Filed: Jun. 8, 2010

(65) Prior Publication Data
US 2010/0244329 A1    Sep. 30, 2010

Related U.S. Application Data

(62) Division of application No. 10/931,853, filed on Aug. 31, 2004, now abandoned.

(51) Int. Cl.
*A61F 2/06* (2006.01)
(52) U.S. Cl. ....................................... 623/1.15; 264/479

(58) Field of Classification Search .................. 623/1.11, 623/1.15, 1.42, 1.46; 264/479
See application file for complete search history.

(56) References Cited

U.S. PATENT DOCUMENTS

| 6,174,329 | B1 | 1/2001 | Callol et al. |
| 6,395,326 | B1 * | 5/2002 | Castro et al. ............. 427/2.24 |
| 2002/0111590 | A1 | 8/2002 | Davila et al. |
| 2003/0083740 | A1 | 5/2003 | Pathak |
| 2004/0093077 | A1 | 5/2004 | White et al. |
| 2004/0147998 | A1 * | 7/2004 | Nolting ..................... 623/1.11 |

OTHER PUBLICATIONS

Rodriguez, Principles of Polymer Systems $2^{nd}$ ed., McGraw Hill (1982).

* cited by examiner

*Primary Examiner* — Victor Nguyen
(74) *Attorney, Agent, or Firm* — Squire Sanders (US) LLP

(57) ABSTRACT

A medical device and methods of making the medical device such as a stent having selected regions with different material properties than other regions are disclosed. Selection and modification of the regions may be based on facilitating a desired mechanical behavior and/or therapeutic prophylactic property of the device.

19 Claims, 5 Drawing Sheets

FIG. 1B  FIG. 2A

METHOD OF MAKING A MEDICAL DEVICE WITH REGIOSELECTIVE STRUCTURE-PROPERTY DISTRIBUTION

This application is a divisional application of application Ser. No. 10/931,853 filed Aug. 31, 2004, now abandoned, and is incorporated by reference herein.

BACKGROUND OF THE INVENTION

1. Field of the Invention

This invention relates to implantable medical devices and methods of making such devices that have selected regions with different material properties than other regions of the device.

2. Description of the State of the Art

This invention relates to generally to medical devices having regions with different clinical or therapeutic and mechanical requirements. Therefore, the invention may be applied to a diverse array of medical devices, including, but not limited to radial expandable endoprostheses, heart valves, bone screws, and suture anchors. For example, radially expandable endoprostheses are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involved compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

The structure of stents is typically composed of scaffolding that includes a pattern or network of interconnecting structural elements or struts. The scaffolding can be formed from wires, tubes, or sheets of material rolled into a cylindrical shape. The scaffolding is designed to allow the stent to be radially expandable. The pattern should be designed to maintain the longitudinal flexibility and radial rigidity required of the stent. Longitudinal flexibility facilitates delivery of the stent and radial rigidity is needed to hold open a bodily lumen.

Stents have been made of many materials such as metals and polymers, including biodegradable polymer materials. A medicated stent may be fabricated by coating the surface of either a metallic or polymeric scaffolding with a polymeric carrier that includes an active agent or drug. Polymeric scaffolding may also serve as a carrier of an active agent or drug. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers may be configured to meet this additional clinical requirement since they may be designed to completely erode after the clinical need for them has ended.

Conventional methods of constructing a stent from a polymer material involves extrusion of a polymer tube based on a single polymer or polymer blend and then laser cutting a pattern into the tube. A potential shortcoming of such methods is that material properties of the stent formed by such methods tend not to vary substantially throughout different regions of the stent. Conventional methods of fabricating metallic stents suffer from the same shortcoming. Material properties may include mechanical and thermal properties. Additional material properties may also include the absorption rate of a biodegradable stent material and the composition of polymer and active agents or drugs impregnated into a polymer scaffolding. In addition, conventional coating methods also tend to form coatings that have relatively uniform material properties along the surface of a stent.

Due to certain mechanical and clinical requirements, it may be advantageous for certain material properties to be different in different portions of an implantable medical device. It may be desirable for some portions of a stent to have some mechanical properties, absorption rates, and composition different than in other portions of the device. For example, as indicated above, localized regions of a stent may have different mechanical requirements due to relatively high stress and strain during use, and, thus may require different mechanical properties for the different regions.

SUMMARY OF THE INVENTION

Various embodiments of the present invention include a method of manufacturing a stent, comprising: selectively heating a selected region of a stent made of a polymer to modify a material property in the selected region of the stent that has a variable strain profile under applied stress, wherein the modification accommodates the variable strain profile of the stent by reducing or preventing mechanical instability when the stent is under applied stress, and wherein the stent is composed of a scaffolding including a network of interconnecting struts.

BRIEF DESCRIPTION OF THE DRAWINGS

FIGS. 2A-C, 3A-3B, and 4A-B depict portions of a stent.

DETAILED DESCRIPTION OF THE INVENTION

Figure 1A:
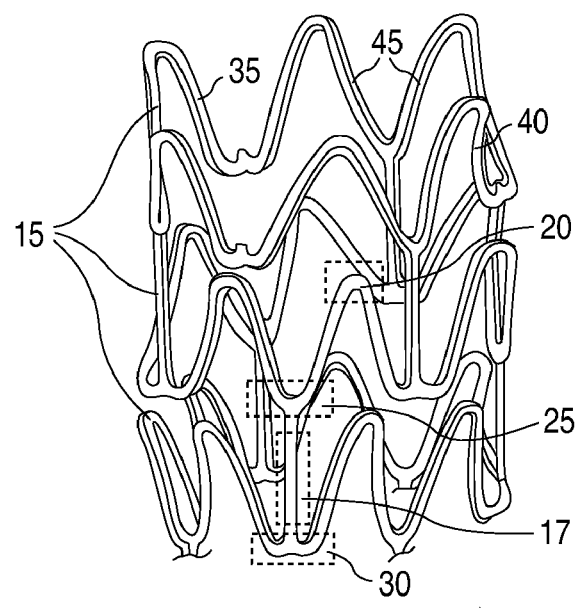
FIG. 1 depicts a stent.

For the purposes of the present invention, the following terms and definitions apply:

The "glass transition temperature," $T_g$, is the temperature at which the amorphous domains of a polymer change from a brittle vitreous state to a solid deformable state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in volume and/or length). In addition, compressive stress is a normal component of stress applied to materials resulting in their compaction (decrease in volume and/or length). Stress may result in deformation of a material, which refers to change in length and/or volume. "Expansion" or "compression" may be defined as the increase or decrease in length and/or volume of a sample of material when the sample is subjected to stress. "Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of deformation with applied stress is the modulus. "Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches an "ultimate tensile strength" which refers to the maximum tensile stress which a material will withstand prior to fracture. The ultimate tensile strength is calculated from the maximum load applied during a test divided by the original cross-sectional area. Similarly, "ultimate compressive strength" is the capacity of a material to withstand axially directed pushing forces. When the limit of compressive strength is reached, a material is crushed.

The term "elastic deformation" refers to deformation of an object in which the applied stress is small enough so that the object moves towards its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation. "Elastic limit" refers to the maximum stress that a material will withstand without permanent deformation. "Ultimate strain" is the strain at the elastic limit. The term "plastic deformation" refers to permanent deformation that occurs in a material under stress after elastic limits have been exceeded.

"Elasticity" refers to the ability of a material to deform without failure when subjected to an applied stress. For example, as a temperature of a polymer is increased from below to above its $T_g$, its elasticity increases. The elasticity of the polymer increases from a relatively inelastic state to more elastic states. Polymers that have a relatively high elasticity are flexible and have a relatively low modulus. Conversely, polymers with relatively low elasticity tend to be brittle and have a relatively high modulus. Elasticity is, accordingly, a relative term. Between two polymers, whichever one has the lower modulus has the higher elasticity.

"Neutral axis" refers to a line or plane in a member subjected to a stress at which the strain is zero. For example, a beam in flexure due to stress (e.g., at a top face) has tension on one side (e.g., the bottom face) and compression on the other (e.g., the top face). The neutral axis lies between the two sides at a location or locations of zero strain. The neutral axis may correspond to a surface. If the beam is symmetric (in both geometry and materials) the neutral axis is at the geometric centroid (center of mass) of the beam. The strain increases in either direction away from the neutral axis.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure.

Embodiments of medical devices described herein relate to medical devices having selected regions with mechanical and/or therapeutic or prophylactic requirements different from other regions of the device. Therefore, such selected regions may have desired mechanical behavior and/or therapeutic or prophylactic properties different from the other regions of the device. A therapeutic or prophylactic property refers to a therapeutic or prophylactic effect on a portion of a body arising from an active agent. An active agent can be any substance capable of exerting a therapeutic or prophylactic effect. These devices may include a diverse array of medical devices, including, but not limited to implantable medical devices such as radial expandable endoprostheses, heart valves, and bone screws and other medical devices such as suture anchors.

For example, an implantable medical device may include an underlying scaffolding or substrate. The substrate may have a polymer-based coating with a therapeutic or prophylactic property. The polymer-based coating may contain, for example, an active agent or drug for local administration at a diseased site. The underlying substrate that is coated can be polymeric, metallic, ceramic, or made from any suitable material. Implantable medical device is intended to include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

To fabricate a conventional coating, a polymer, or a blend of polymers, can be applied on the stent using techniques known to those having ordinary skill in the art. For example, the polymer can be applied to the stent by dissolving the polymer in a coating solvent, or a mixture of solvents, and applying the resulting solution on the stent by spraying, "ink-jet-type" deposition methods, brushing, plasma deposition, and the like.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate, coat, or modify an implantable medical device include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ε-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

As indicated above, selected regions of a medical device may have desired mechanical behavior and/or therapeutic or prophylactic properties different from the other regions of the device. Therefore, it may be desirable for the selected regions to have certain properties different from other regions of the medical device. These material properties may include mechanical properties such as modulus and strength. Certain regions of a stent may have relatively high stress and strain when the device is under an applied stress during use, and thus may have different mechanical requirements than regions that experience relatively low stress and strain. In addition, for biodegradable devices, it may be advantageous to have localized regions of a device with different absorption rates than other regions. Furthermore, due to certain therapeutic or prophylactic requirements, it may be desirable for selected regions of a device to have a concentration and/or types of active agents different from other regions. Certain embodiments of a medical device are disclosed herein that may include at least one selected region having a desired mechanical behavior and/or therapeutic or prophylactic property different than other regions of the device. At least one selected region may have been selectively modified to have a material property different than the other regions to facilitate the desired mechanical behavior and/or therapeutic property.

In one embodiment, a desired mechanical behavior may include a desired resistance to mechanical instability to accommodate a variable strain profile in the device when under an applied stress during use. Mechanical instability may include failure of the substrate or coating that may include tearing or fracture and/or detachment of the coating from the surface of the device. In another embodiment, a desired mechanical behavior may include a desired rate of degradation and failure. In another embodiment, a desired therapeutic or prophylactic property may include a treatment with a desired concentration or types of active agent of a bodily region adjacent to a selected region.

The material properties in selected regions may be modified by selectively heating and/or selectively applying a material to a selected region of the device. Selectively applying a material may include forming a coating. In particular, selective application of heat may modify mechanical properties of a selected region of a device. Selectively applying a material may modify properties of a selected region including, but not limited to, mechanical properties such as modulus and strength; types and concentration of active agents; and absorption rate.

Medical devices are typically subjected to stress during use, both before and during treatment. "Use" includes manufacturing, assembling (e.g., crimping a stent on balloon), delivery of a stent through a bodily lumen to a treatment site, and deployment of a stent at a treatment site. Both a scaffolding or substrate and a coating on a scaffolding experience stress that result in strain in the scaffolding and/or coating. For example, during deployment, the scaffolding and/or coating of a stent can be exposed to stress caused by the radial expansion of the stent body. In addition, the scaffolding and/or coating may be exposed to stress when it is mounted on a catheter from crimping or compression of the stent. These stresses can cause the scaffolding and/or coating to fracture and the coating to tear and/or detach from the scaffolding. Failure of the mechanical integrity of the stent while the stent is localized in a patient can lead to serious risks for a patient. For example, there is a risk of embolization caused by a piece of the polymeric scaffolding and/or coating breaking off from the stent.

Generally, the stress and the resulting strain throughout the structure of a stent are not the same throughout the stent. As indicated above, localized portions of the stent's structure undergo substantial deformation. It follows that the degree of stress and strain experienced by various portions of the device may be across a broad spectrum. Some portions may experience no or substantially no stress and strain, while other portions may experience relatively high stress and strain. Additionally, some regions may experience tensile stress and strain, while others may experience compressive stress and strain. In general, it is advantageous for regions of a stent that experience relatively high stress and strain during use to be more elastic or flexible than regions that experience relatively low stress and strain.

It is important for a device to be mechanically stable throughout the range of stress and strain experienced throughout the manufacturing, assembly, and particularly during radial adjustment for a stent. Unfortunately, many polymers used for stent scaffoldings and coatings, are relatively brittle or inelastic at biological conditions. This is particularly true for polymers with a $T_g$ above a body temperature. In this case, the polymer in the stent never reaches its $T_g$, and therefore, the polymer remains relatively inelastic while in the body.

Polymeric stent scaffoldings and/or coatings having a high drug loading are especially vulnerable to fracture during and after deployment. Also, active agents impregnated in the polymer can adversely affect the mechanical properties and therefore the ultimate performance of the polymeric coating on the stent. Active agents tend to increase the crystallinity of a polymer scaffolding and/or coating. As a result, elasticity of the scaffolding and/or coating may be decreased which makes the scaffolding and/or coating more susceptible to failure when subjected to high stress.

However, it may be desirable for certain regions of a device to be relatively stiff or inelastic (high modulus) and strong. Such regions may experience relatively low stress and strain during use, but act as support members that maintain the structural integrity of the device.

It is important for the stent as a whole, as well as individual regions of the stent, to remain mechanically stable throughout the range of stress and strain experienced throughout the treatment process. As indicated above, mechanical instability may include fracture of the scaffolding and/or coating, tearing of the coating, and/or detachment of the coating from the scaffolding.

Furthermore, polymer-based scaffoldings and/or coatings may be particularly vulnerable to mechanical instability during use of an implantable medical device. Polymers, in general, and many polymers used in scaffoldings and coatings for devices tend to have a relatively high degree of inelasticity, and, hence have relatively low strength compared to a metal. Polymers can have an ultimate strain as low as 5% of plastic strain. In general, the ultimate strain for a polymer is highly dependent on material properties including percent crystallinity, orientation of polymer chains, and molecular weight. Therefore, polymer-based scaffoldings and/or coatings are highly susceptible to fracture, tearing, and/or detachment at regions of a medical device subjected to relatively high stress and strain.

Embodiments described herein may be illustrated by a stent. FIG. 1A depicts an example of a three-dimensional view of a stent 10. The stent may have a pattern that includes a number of interconnecting elements or struts 15. The embodiments disclosed herein are not limited to stents or to the stent pattern illustrated in FIG. 1A. The embodiments are easily applicable to other patterns and other devices. The variations in the structure of patterns are virtually unlimited. As shown in FIG. 1A the geometry or shape of stents vary throughout its structure. A pattern may include portions of struts that are straight or relatively straight, an example being a section 17. In addition, patterns may include struts that include curved or bent portions as in a section 20. Patterns may also include intersections of struts with curved or bent portions as in sections 25 and 30.

Additionally, a surface of a medical device may also be characterized by the relative location of the surface with respect to a bodily lumen. The device may include luminal surfaces or outer portions, abluminal surfaces or inner portions, and surfaces between the luminal and abluminal surfaces. For example, struts 15 of stent 10 include abluminal faces or surfaces 35, luminal faces or surfaces 40, and sidewall faces or surfaces 45. A strut may also be described by axes, a latitudinal axis, and a longitudinal axis. FIG. 1B depicts a portion 54 of a strut depicting a latitudinal axis 50 and a longitudinal axis 55 along a straight section of portion 54. A longitudinal axis 51 on a curved section of a strut may be defined as a tangent to a curvature at a location on the curved section. A corresponding latitudinal axis 56 is perpendicular to longitudinal axis 56. In other embodiments, the latitudinal cross-section may include any number of faces or be a curved surface. In some embodiments, the latitudinal cross-section may include any number of faces or be a curved surface.

The pattern that makes up the stent allows the stent to be radially expandable and longitudinally flexible. Longitudinal flexibility facilitates delivery of the stent and radial rigidity is needed to hold open a body lumen. The pattern should be designed to maintain the longitudinal flexibility and radial rigidity required of the stent.

As indicated above, the stress and strain experienced by a medical device when under an applied stress during use is not uniform throughout the scaffolding and/or the coating. For instance, the stress and strain experienced by a stent in a radially expanded state are different in various portions of the stent. Some portions of a stent pattern may have no or relatively no strain, while others may have relatively high strain. Straight or substantially straight sections of struts such as section 17 of stent 10 in FIG. 1 experience no or relatively no strain. However, sections 20, 25, and 30 may experience relatively high strain when the stent is expanded or crimped.

Figure 2C:
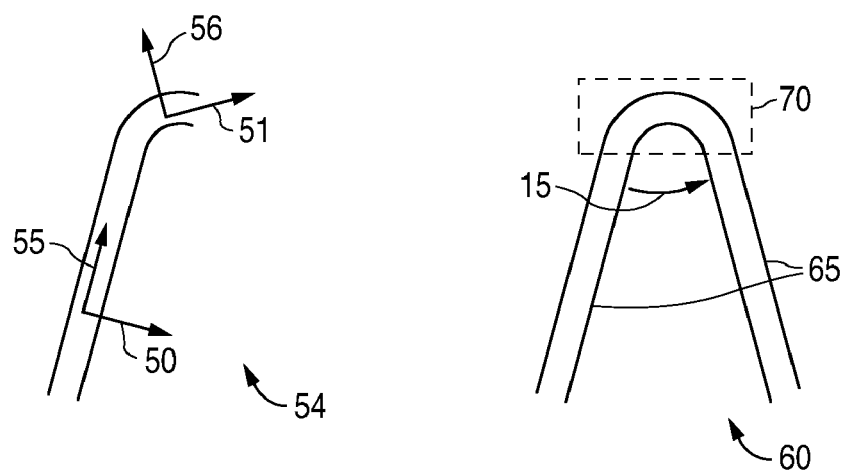
Figure 2C:
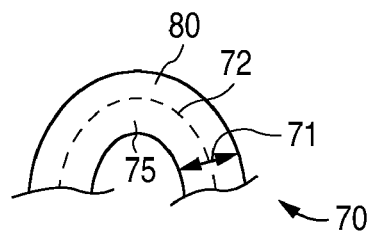
Figure 2B:
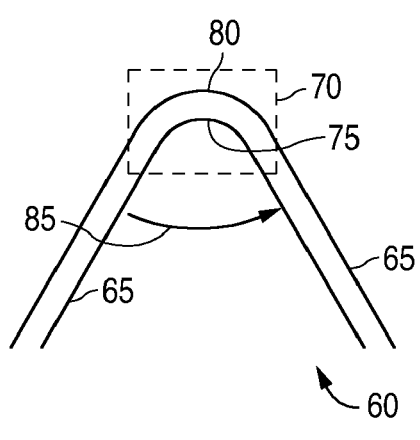

FIGS. 2A-C, 3A-B, and 4A-B depict partial planar side views of luminal or abluminal surfaces from a stent. The figures illustrate the nonuniformity of stress and strain in a medical device. FIG. 2A depicts a partial planar side view of a portion 60 from a stent in an unexpanded state that includes straight sections 65 and a curved section 70 with an angle 85. When a stent undergoes radial expansion, portions of struts bend resulting in an increase of angle 85 between straight sections 65, as shown in FIG. 2B. FIGS. 2A and 2B depict portion 60 in a plane of bending. The bending of portion 60 causes no or substantially no strain in straight sections 65. However, the bending of section 60 causes relatively high stress and strain in most of curved section 70. A concave portion 75 of curved section 70 experiences relatively high tensile stress and strain and a convex portion 80 of curved section 70 experiences relatively high compressive strain. When a stent is crimped, angle 85 decreases and concave portion 75 experiences relatively high compressive strain and convex portion 80 experiences relatively high tensile strain. FIG. 2C depicts an expanded view of curved section 70 with a neutral axis 72 indicated. The strain along the neutral axis is zero. In the stent, the neutral axis corresponds to a surface of zero strain. For a strut that is symmetric along its longitudinal and latitudinal axis, the neutral axis may be a geometric centroid perpendicular to a plane of bending (i.e., perpendicular to the plane of the sheet of paper). In the case of portion 70 in FIG. 2C, neutral axis 72 runs along the midpoint or center of a latitudinal width 71 of curved section 70. Therefore, in a small, narrow region of curved section 70 along neutral axis 72, there is zero or relatively low strain.

Figure 3A:
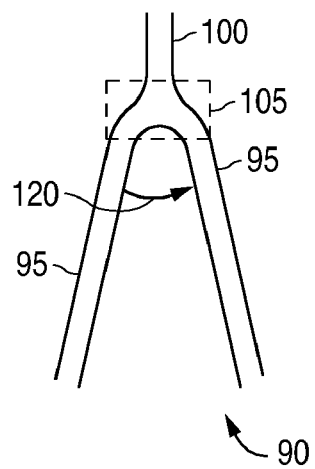
Figure 3B:
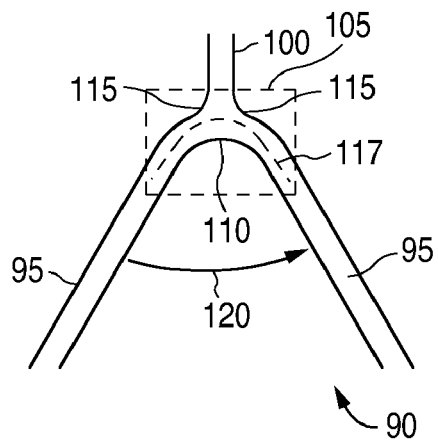

FIG. 3A depicts a partial planar side view of a portion 90 from a stent in an unexpanded state that includes curved section 105, straight sections 95 at an angle 120, and straight section 100. As shown in FIG. 3B, radial expansion of the stent increases angle 120. The stress and strain in straight sections 95 and 100 is relatively small. Section 105 experiences relatively high tensile stress and strain at concave portion 110 and relatively high compressive stress and strain at portion 115. A neutral axis 117 is a surface of zero strain that is the boundary between portion 110 and portion 115.

Figure 4A:
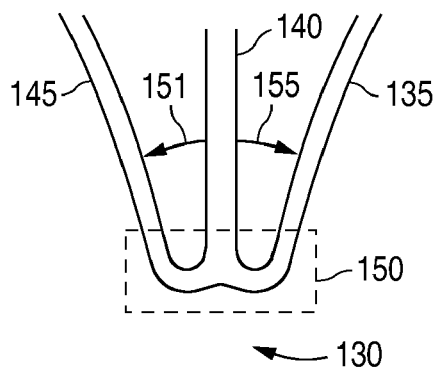
Figure 4B:
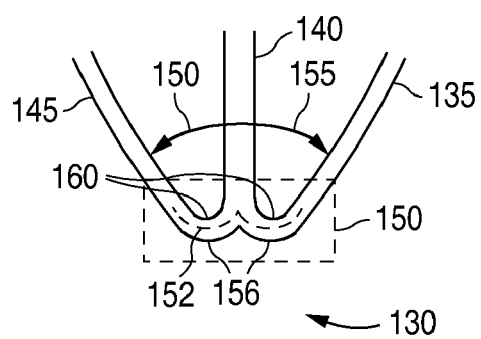

FIG. 4A depicts a partial planar side view of a portion 130 from a stent in an unexpanded state that includes curved section 150, straight sections 135, 140, and 145. Straight sections 135 and 140 are at an angle 155 and straight sections 140 and 145 are at an angle 151. As shown in FIG. 4B, radial expansion of the stent increases angles 150 and 155. The stress and strain in straight sections 135, 140, and 145 is relatively small. Section 150 experiences relatively high tensile stress and strain at concave portions 160 and relatively high compressive stress and strain at convex portions 156. A neutral axis 152 is a surface of zero strain that is the boundary between portions 156 and portions 160. The description and analysis relating to nonuniformity of stress and strain in a medical device is not limited to the structures in FIGS. 2A-C, 3A-B, and 4A-B. Analysis of strain distribution in a device, or generally any structure, subjected to applied stress may be performed for a device or structure of virtually any geometry.

In general, material properties, including certain mechanical properties, may be modified by heating a material. In particular, heating polymer materials may increase or decrease the modulus of the material. Increasing the modulus of a polymer may make the polymer stiffer and stronger, while decreasing the modulus may make the polymer more flexible or less brittle. The modification of mechanical properties in polymers due to heating is due to alteration of the degree of crystallinity and/or size of crystalline regions in a polymer material. Typically, a higher degree of crystallinity and/or a greater size of crystalline regions in a polymer material correspond to a higher modulus and higher strength of the material. Conversely, the more amorphous a polymer material is, the lower the modulus, and hence the more flexible the polymer material is.

Furthermore, the manner of modification depends on the temperature range to which a polymer material is heated. Heating a polymer material to a temperature below the $T_g$ of the polymer does not significantly alter the molecular structure, and hence, the mechanical properties of the material. Below $T_g$, energy barriers to segmental motion of the chains of a polymer inhibit or prevent alteration of molecular structure of a polymer material.

Figure 5:
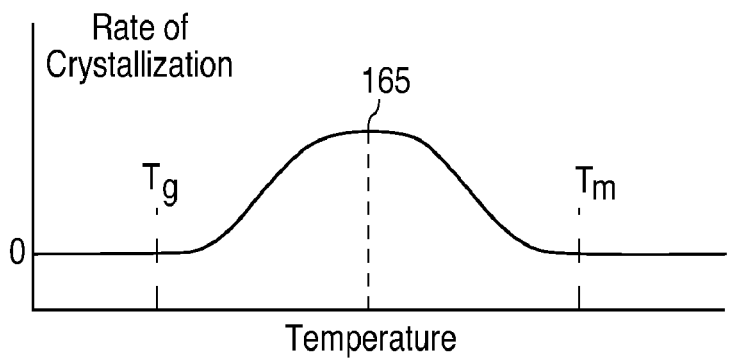
FIG. 5 depicts a schematic plot of the rate of crystallization of a polymer as a function of temperature.

In general, crystallization may occur in a polymer material that is heated to a temperature between $T_g$ and the melting temperature, $T_m$, of the polymer. As a result, heating a polymer to a temperature between the $T_g$ and the $T_m$ of the polymer increases the modulus of the polymer, which makes it stiffer. FIG. 5 depicts a schematic plot of the rate of crystallization of a polymer as a function of temperature. (Rodriguez, F., *Principles of Polymer Systems*, $2^{nd}$ ed., McGraw Hill (1982)) FIG. 5 shows that the rate of polymer crystallization increases as the temperature is increased from below the $T_g$ of the polymer or is decreased from above the $T_m$ of the polymer. The rate of crystallization reaches a maximum 165 somewhere between the $T_g$ and the $T_m$. FIG. 5 shows that effectively no crystallization occurs below the $T_g$ or above the $T_m$.

In addition, as indicated above, an amorphous polymer may be formed by heating a polymer material. Above the $T_m$, a polymer material is a disordered melt and cannot crystallize and any crystallinity present is destroyed. Quenching a polymer heated to above the $T_m$ to a temperature below the $T_g$ of the polymer may result in the formation of a solid amorphous polymer. The resulting amorphous polymer material may have a lower modulus and be a more flexible or a less stiff material than before heating.

Therefore, certain embodiments of a method of manufacturing an implantable medical device may include selectively heating a selected region of a device to modify a material property of the selected region of the device having a variable strain profile under applied stress. The selective heating may facilitate a desired resistance to mechanical instability to accommodate the variable strain profile on the device so as to reduce or prevent mechanical instability as compared to other regions on the device that have not been selectively heated. In some embodiments, the selective application of heat may selectively modify material properties of the selected region including, but not limited to, a tensile and/or compressive strength, a tensile or compressive modulus, thermal properties, and/or absorption rate of a bioabsorbable polymer in the region.

In some embodiments, the region may be as small 20 microns in diameter, or more narrowly as small as 30, 40, 50, or 60 microns in diameter. In some embodiments, the selected region may include a coating on the device.

In some embodiments, a selected region may be selectively heated with a controlled heating system which is described herein. In one embodiment, a controlled heating system may include a laser for heating a selected region. Representative examples of lasers that may be used include, but are not limited to, excimer, carbon dioxide, and YAG lasers. In other embodiments, a selected region may be heated with conduction or convention. For example, a heated filament may be disposed proximate to or in contact with a selected region. The parameters of a heating method may be used to control characteristics of a heated region including, but not limited to, the temperature, size, shape, and thickness. For example, the parameters of laser heating may include, but are not limited to, the length of a pulse, energy of the beam, and/or cross-sectional size of beam. In addition, the conductive heating parameters may include, but are not limited to, the temperature of a heated filament, size of a heated filament, heated filament material, and distance of heated filament from region.

In certain embodiments, the device may be a stent including a pattern of struts that were formed by laser cutting the pattern into a tube. Heat may be selectively applied prior to, contemporaneous with, and/or subsequent to laser cutting the pattern into the tube. It may be desirable to selectively apply heat prior to forming the pattern in the case of a fine, intricate stent pattern that has relatively thin struts. Selectively applying heat prior to forming a pattern may inhibit or prevent damage to such fine struts. In addition, selectively applying heat contemporaneous with forming the pattern may increase manufacturing efficiency.

Furthermore, selective heating may increase the temperature of the selected region to within a range of temperature that material properties are altered. In one embodiment, the heating may increase the temperature to greater than or equal to the $T_g$ of the polymer and less than or equal to the $T_m$ of the polymer. Other embodiments may include increasing the temperature of the selected region with the applied heat to greater than the $T_m$ of the polymer. As indicated by the above discussion, the temperature to which the selected region is heated depends on the desired modification of a material property.

In some embodiments, modifying a material property in a selected region of the device may include decreasing the tensile and/or compressive modulus. As indicated above, the tensile and/or compressive modulus of the selected region may be decreased by increasing the temperature of the selected region to greater than or equal to the $T_m$ of the polymer. The temperature of the region may then be decreased to a temperature below the $T_g$ of the polymer. In certain embodiments, the temperature may be decreased by allowing the region to cool through contact with the environment at an ambient temperature after heating the region. Other embodiments may include blowing an inert gas such as air, oxygen, nitrogen, etc. that is less than or equal to an ambient temperature. A heated selected region may cool rapidly to below the $T_g$ of the polymer once heating stops due to a small size of the heated region. In some embodiments, the rate of cooling may influence the degree of amorphous molecular structure induced in the selected region. Allowing the region to cool to a temperature between the $T_g$ and $T_m$ of the polymer may result in at least some crystallization in the region. The polymer material may then be quenched to below the $T_g$ from that temperature. Therefore, the degree of flexibility induced in the region may be controlled. In some embodiments, the cooling rate may be reduced, for example, by blowing a heated inert gas on the region or cooling the region in a heated fluid.

Figure 6:
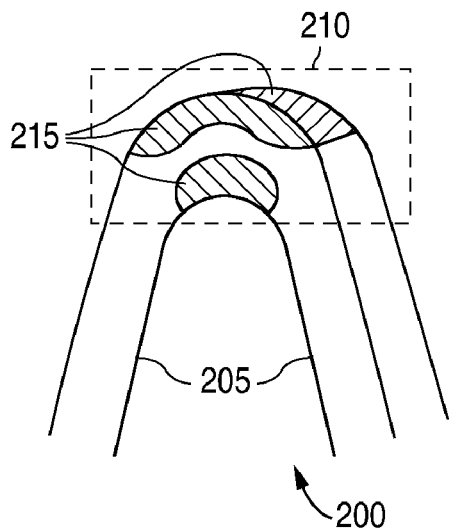
FIGS. 6-7 depict portions of a stent modified by selective application of heat.

Furthermore, it may be desirable to decrease the tensile and/or compressive modulus, and thus increase flexibility or decreasing stiffness, of a selected region of a device that has a higher strain than other regions of the device when the device is placed under an applied stress during use. For example, as indicated in FIGS. 2A-C, 3A-B, and 4A-B, different regions of a strut on a stent experience different levels of stress and strain during use. For example, a selected region including at least a portion of a curved or bent portion of a strut may be selectively heated to decrease the tensile and/or compressive modulus. FIG. 6 depicts section 200 of a stent with a curved portion 210, similar to that shown in FIGS. 2A-C, with struts 205. Heat may be applied selectively to shaded regions 215 to decrease the tensile and/or compressive modulus, making the regions more flexible. Shaded regions 215 may include portions of abluminal, luminal, and/or side-wall surfaces of portion 210. In a similar manner, at least a portion of portion 105 in FIGS. 3A-B and at least a portion of portion 150 in FIGS. 4A-B may be selectively heated to decrease the tensile and/or compressive modulus. In general, according to the methods described herein, the modulus of any region may be decreased, which increases the flexibility or decreases the stiffness of the region, by selective heating at and/or proximate to the region.

In some embodiments, modifying a material property in a selected region of the device may include increasing the tensile and/or compressive modulus. As indicated above, the tensile and/or compressive modulus of the selected region may be increased by increasing the temperature of the selected region to greater than or equal to the $T_g$ of the polymer in the region and less than or equal to the $T_m$ of the polymer. The temperature of the region may then be decreased to a temperature below the $T_g$ of the polymer. Since the crystallization rate of a polymer depends on the temperature between the $T_g$ and the $T_m$ as illustrated in FIG. 5, the degree of modification of material properties of a polymer material may be controlled by controlling the temperature of the region. For example, heating the selected region to a temperature at or near the maximum rate of crystallization of the polymer may induce more crystallization in the region, resulting in a stiffer, higher modulus region. In addition, the degree of induced crystallization may also be controlled by the rate of cooling of the region.

Figure 7:
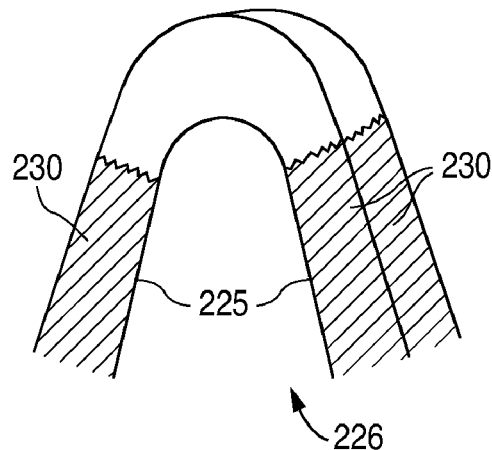

It may be desirable to increase the tensile and/or compressive modulus, and thus increase stiffness or decrease flexibility, of at least a portion of a section of a device that has a lower strain than another section of the device when the device is placed under an applied stress during use. For example, at least a portion of straight or relatively straight portion of a strut may be selectively heated to increase the tensile and/or compressive modulus. FIG. 7 depicts portion 220 of a stent with struts 225. The tensile and/or compressive modulus of the shaded portions of struts 220 may be increased by selective application of heat. Shaded regions 220 may include portions of abluminal, luminal, and/or side-wall surfaces. Generally, the methods described herein may be used to increase the modulus, and hence increase stiffness or decrease flexibility, of a selected region by selective heating.

Furthermore, as indicated above, certain embodiments of a medical device may include at least one selected region of a device having a desired therapeutic or prophylactic property different from other regions of the device during use. Some embodiments may include a coating selectively applied on the device to facilitate the desired therapeutic property of at least one selected region of the device. In an embodiment, a coating may be selectively applied to selected region of a medical device using a controlled deposition system described herein. The system may deposit a coating on any region of a stent, which may be as small as 50 microns, or more narrowly as small as 25 microns.

In some embodiments, the desired therapeutic or prophylactic property may be a treatment with a desired concentration or types of active agents of a bodily region adjacent to the selected region. For instance, therapeutic or prophylactic treatment of a lesion in a lumen using a stent may be facilitated by having a concentration of active agents and/or types of active agents on selected regions that are different than other regions. The bodily region adjacent to the selected region may be treated by the desired types of active agent at a desired concentration in a coating on the selected region. For example, in long lesions, the center portion of the lesion may be more diseased than the ends of the lesion. The center of the lesion may require more of an active agent or specific types of active agents than the ends of the lesion. Therefore, a coating on a center portion of a stent may have the desired active agents with a desired concentration.

Figure 8:
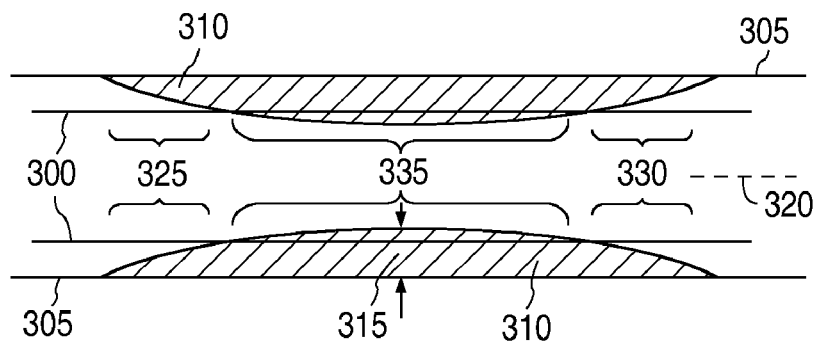
FIG. 8 depicts a stent in a bodily lumen.

FIG. 8 depicts a schematic illustration of a stent 300 deployed in a lumen 305. Stent 300 is deployed in lumen 305 at the site of a lesion 310. A thickness 315 of lesion 310 varies along an axis 320 of lumen 305. FIG. 8 shows that lesion 310 is thickest at a center portion of the lesion and thinner at the end portions of the lesion. Therefore, it may be desirable to have a higher concentration of active agent or drug at center portion 335 of stent 300 than end portions 325 and 330. In addition, center portion 335 may require different type(s) of active agents or drugs than end portions 325 and 330.

Additionally, some embodiments of a medical device may include at least one selected region of a device having a desired rate of degradation and failure different from other regions of the device. In certain embodiments, at least one selected region may be selectively coated so that a coating on at least one selected region has an absorption rate different from a coating on the other regions to facilitate the desired rate of degradation and failure.

Some embodiments may include a coating on at least one selected region having an absorption rate greater than the other regions. For example, in certain embodiments, a biodegradable stent having different absorption rates on some regions may degrade and fail in a more desirable manner. As discussed above, a bioabsorbable stent is intended to remain in the body for a limited duration of time until its intended purpose has ended. Relatively small particles and/or molecules of stent material are eroded, absorbed, or resorbed due to degradation by bodily fluids and then are carried away by the bodily fluid. Degradation, erosion, absorption, and resorption of stent material result in degradation of the mechanical properties of the stent. The degradation of stent material may cause mechanical failure which may result in structural-sized portions of the stent separating from one another. The presence of such structural-sized portions may cause problems in a bodily lumen such as thrombosis and blockage. The smaller the size of such portions and the more uniform the mechanical failure of the stent, the lower the risk of such complications. Therefore, it may be advantageous to fabricate a stent that fails in a predictable and desirable manner.

In one embodiment, a relatively fast eroding coating may include, but is not limited to, poly(DL-lactide-co-glycolide). Poly(DL-lactide) is slower eroding than poly(DL-lactide-co-glycolide). A relatively slow eroding coating may include, but is not limited to, poly(L-lactide), which is slower eroding than poly(DL-lactide).

In one embodiment, a stent may be fabricated having at least one region that is relatively weak and susceptible to failure within a certain range of applied stress. For example, the weak regions(s) may be portions of struts that are thinner than struts in other regions of the stent. The applied stress may correspond to conditions that a stent undergoes during use. The weak region(s) may then be coated with a bioabsorbable polymer with an absorption rate that is greater than the absorption rate of a other regions of the stent. The coating may increase the strength of the weak region(s) to withstand the applied stress of the stent during use.

Figure 9:
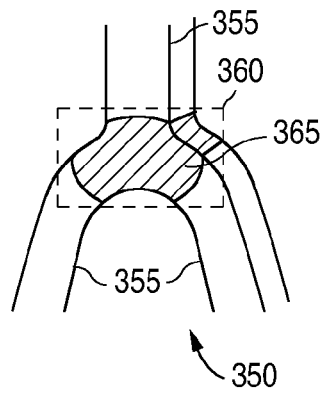
FIGS. 9-10 depict portions of a stent.

In one embodiment, coated weak regions may be a plurality of regions at or proximate to intersections of at least two struts of the stent, for example, portions 25 and 30 in FIG. 1. FIG. 9 illustrates portion 350 of a strut with struts 355 that includes a region 360 of interconnection of struts 355. Region 360 is selectively coated, for example, in shaded region 365 with a coating that has a faster absorption rate than struts 355. Region 365 may include portions of the abluminal, luminal, and sidewall surfaces in region 360.

In other embodiments, at least one region may have a coating with a slower absorption rate than other regions of the device. In some embodiments, the other regions may also have a coating. The coating on at least one region may act to inhibit or delay degradation of the mechanical properties of the first section. Since other regions may degrade faster, the mechanical properties may also degrade at a faster rate, potentially resulting in mechanical failure of the other regions before at least on region with a slower degradation rate. The other regions may correspond to regions at or proximate to the intersection of at least two struts of the stent.

As discussed above, different regions of a medical device may have different mechanical requirements. Certain embodiments of a medical device may include at least one selected region of a device having a different resistance to mechanical instability than other regions of the device due to a variable strain profile of the device when under applied stress during use. Mechanical instability may include failure of the substrate or coating that may include tearing or fracture and/or detachment of the coating from the surface of the device. The material selectively applied to at least one selected region may accommodate the variable strain profile.

In some embodiments, at least one selected region may have a higher strain than the other regions when the device is under an applied stress during use. It may be desirable for at least one selected region to have a higher elasticity, or lower modulus than other regions of the device. A region with a higher elasticity may have a greater resistance to mechanical stability than the other regions.

In one embodiment, the selectively applied material may include a plasticizer that lowers the modulus of at least one selected region. In some embodiments, the material may include a polymer with a lower modulus than other regions of the device. In other embodiments, the selectively applied material may be a coating with a lower modulus than a coating on other regions of the device. For example, the coating may have a primer layer and a reservoir layer.

A relatively flexible, low modulus polymer may include, but is not limited to, poly(L-lactide-co-ϵ-caprolactone). A relatively stiff, high modulus polymer may include, but is not limited to, poly(L-lactide) and poly(glycolide).

Figure 10:
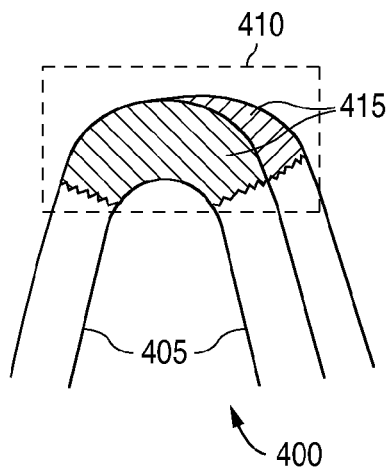

As discussed above and illustrated in FIGS. 2A-C, 3A-B, 4A-B, at least one selected region may correspond to a curved or bent portion of a strut and other regions may correspond to a straight or relatively straight portion of a strut. The mechanical instability may include fracture of the coating and/or detachment of the coating from a surface of the first section. A coating with a greater resistance to mechanical instability may include, but is not limited to, a greater resistance to strain, a lower tensile and/or compressive modulus (greater flexibility or elasticity), and better adhesion properties. FIG. 10 depicts a portion 400 of a stent similar to that shown in FIGS. 2A-C. Portion 400 includes struts 405 and a curved portion 410. Curved portion 410 is selectively coated in shaded region 415, which may include abluminal, liminal, and sidewall surfaces of portion 410.

As indicated above, it may be desirable for certain regions of a device to be relatively stiff or inelastic (high modulus) and strong. Therefore, the coating may include a relatively high modulus polymer such as poly(L-lactide) or poly(glycolide). Such regions may experience relatively low stress and strain during use, but act as support members that maintain the structural integrity of the device. Therefore, it may be desirable to selectively apply a coating with a relatively high modulus and/or strength on such regions.

In some embodiments, the selectively applied material on at least one selected region may include a polymer, a plasticizer, a primer, a solvent, and/or a bioactive agent or drug. For instance, the coating may be polymeric carrier for a bioactive agent for use in delivery of the agent to a diseased site in a lumen. In addition, a plasticizer in coating may increase the flexibility of the coating. Also, a drug delivery coating with primer layer may improve the adhesion properties of a coating, inhibiting or preventing fracture and/or detachment of the coating form the surface of a substrate. However, it may be desirable to limit the use of different or modified coating material to higher strain portions of the device to limit exposure of such additional components to a body.

In certain embodiments, the coating on the at least one selected region may inhibit or prevent mechanical instability of a substrate of a medical device. The coating may include a relatively flexible, low modulus, elastomeric polymer such as poly(L-lactide-co-trimethylene carbonate), or poly(D,L-lactic acid)-polyethylene glycol-poly(D,L-lactic acid) tri-block copolymer. A relatively flexible polymer coating may inhibit or prevent mechanical instability of a substrate in higher strain regions of a medical device.

Additionally, it may be desirable to have a lower concentration of active agents in a coating in a high strain region of a medical device. It is known that the presence of an active agent in a polymer carrier of a coating tends to increase the crystallinity of the polymer carrier. The increased crystallinity may increase the modulus of the coating which decreases the elasticity of the coating. As the elasticity of the coating decreases the coating becomes more susceptible to fracture and detachment from a substrate. As discussed above, certain regions of a device may experience higher stress and strain than other regions. Therefore, it may be desirable for a selected high strain region to have a lower concentration of active agent than other regions. As discussed above and illustrated in FIGS. 2A-C, 3A-B, 4A-B, a high strain region may correspond to a curved or bent portion of a strut and a second section may correspond to a straight or relatively straight portion of a strut of a stent.

As indicated above, the resistance to mechanical instability may be increased by including a plasticizer in the polymer. In general, a "plasticizer" is a chemical additive that increases the elasticity of a polymer. A plasticizer, which is usually a low molecular weight nonvolatile molecule, can be dissolved with a polymer material before the applying the material to a device. An active agent may also act as a plasticizer.

It is desirable for a plasticizer for use in applying to a medical device to be biocompatible and non-volatile or substantially nonvolatile. Low volatility is important since diffusion of a plasticizer through a vapor phase into other phases or components proximate to an implantable device may influence the effectiveness and safety of the device.

In addition, it is not desirable for a plasticizer to substantially or significantly affect the drug release kinetics or drug stability of active agents in a coating. However, it may be advantageous for a plasticizer to change the degradation rate of a biodegradable polymer in a polymer coating.

In one embodiment, a plasticizer can include low molecular weight oligomers of monomers forming a biodegradable polymer. For example, the oligomer can be a dimer, trimer, tetramer or oligomer of lactic acid, which forms PDLL or poly(D,L-lactic acid) (PDLLA). Some exemplary low molecular weight plasticizers may include cyclic or linear oligomers of glycolic acid, lactic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, and 5-hydroxyhexanoate. Other exemplary plasticizers may include dimers or trimers of lactic acid. Lactic acid can be racemic or enantiomeric in D or L form. In one embodiment, the plasticizer is an oligomer of poly(D,L-lactic acid) (PDLLA) having a molecular weight in the range from 1000 Daltons to 5,000 Daltons. The low molecular weight oligomers can be formed by methods documented in the art (see, for example, see, for example, Michael Smith, Organic Synthesis, $2^{nd}$ Edition, McGraw-Hill, 2001).

In another embodiment, the plasticizer can be a fatty acid. The fatty acid can be synthetic or naturally occurring fatty acids. The fatty acid can be liquid or solid. Representative natural fatty acids include, but are not limited to, palmitoleic acid, lauric acid, oleic acid, linoleic acid, and arachidonic acid. Representative synthetic fatty acids include, for example, C6-C15 alkanoic acids such as heanoic acid, heptanoic acid, or octanoic acid. Additionally, plasticizers may also include esters of the fatty acids. It is believed that fatty acid esters do not influence the polymer degradation kinetics of the coating polymer or stability of the drug in a drug-delivery coating. Representative ester plasticizers may include the ethyl, propyl, and butyl ester of oleic acid. In addition, plasticizers may be a glyceride, such as a mono, di and triglyceride. The glycerides can be natural glycerides or synthetic glycerides and can contain any of the fatty acids described above. For example, most naturally occurring triglycerides contain stearate, palmitate, linoleic, oleic fatty facid, or a mixtures thereof. Further representative plasticizers may include synthetic or naturally occurring fatty alcohols including, but not limited to, fatty alcohols described in the FDA GRAS (generally recognized as safe) list. Additional representative examples of plasticizers may include citric acid esters for poly(L-lactide), lactide or lactic acid monomer such as ethyl lactate, a polyalkylene glycol such as polyethylene glycol (PEG), or a polyalkylene oxide.

Furthermore, as discussed above, the resistance to mechanical stability of a coating on a selected region of a medical device may be increased by enhancing the adhesion properties of the coating. In some embodiments, the resistance to strain of the coating on a selected region may be increased by including at least one primer layer on the first section. In general, a "primer layer" is a coating layer on a surface that improves the adhesion of subsequent coating layers on the surface. In some embodiments, the primer layer may include one or more polymers.

As noted above, the presence of an active agent in a polymeric matrix can interfere with the ability of the matrix to adhere effectively to the surface of the device. Increasing the quantity of the active agent reduces the effectiveness of the adhesion. High drug loadings in the coating can hinder the retention of the coating on the surface of the device. A primer layer can serve as a functionally useful intermediary layer between the surface of the device and an active agent-containing or reservoir coating, or between multiple layers of reservoir coatings. The reservoir layer may include one or more active agents dispersed within one or more polymers. The primer layer provides an adhesive tie between the reservoir coating and the device—which, in effect, would also allow for the quantity of the active agent in the reservoir coating to be increased without compromising the ability of the reservoir coating to be effectively contained on the device during delivery and, if applicable, expansion of the device.

Figure 11A:
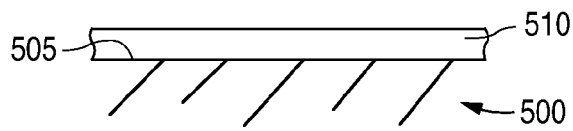
FIGS. 11A-11D illustrate coatings deposited over a surface of an implantable medical device.

Some of the embodiments of polymer coatings are illustrated by FIGS. 11A-D. The figures have not been drawn to scale, and the thickness of the various layers have been over or under emphasized for illustrative purposes. FIG. 11A depicts a substrate of a medical device 500, such as a stent, having a surface 505. A primer layer 510 is deposited on surface 505. The polymer in primer layer 510 may be a homopolymer, copolymer, terpolymer, etc. The polymer may also include random, alternating, block, cross-linked, blends, and graft variations thereof. For instance, primer layer 510 may include a poly(lactic acid).

Figure 11B:
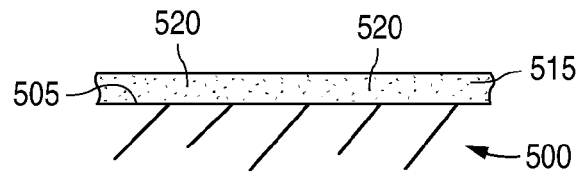

FIG. 11B depicts a reservoir layer 515 deposited on surface 505. The reservoir layer may have a polymer and an active agent 520 dispersed in the polymer. The active agent may be, for example, 40-O-(2-hydroxy)ethyl-rapamycin, known by the trade name of Everolimus, available from Novartis as Certican™. Reservoir layer 515 may release the active agent when substrate 500 is inserted into a biological lumen. Without a primer layer between surface 505 and reservoir layer 515, reservoir layer 515 may be more susceptible to failure as substrate 500 is implanted in a patient for treatment.

Figure 11C:
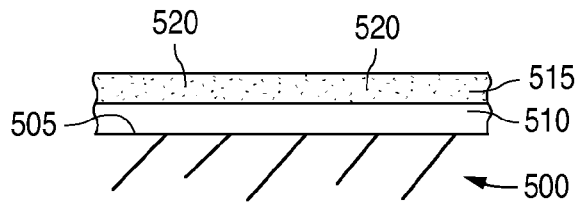

FIG. 11C depicts reservoir layer 515 deposited on primer layer 510. Primer layer 510 serves as an intermediary layer for increasing the adhesion between reservoir layer 515 and surface 505. Increasing the amount of active agent 520 admixed within the polymer can diminish the adhesiveness of reservoir layer 515 to surface 505. Accordingly, using an active agent-free polymer as an intermediary primer layer 510 allows for a higher active agent content for reservoir layer 515.

Figure 11D:
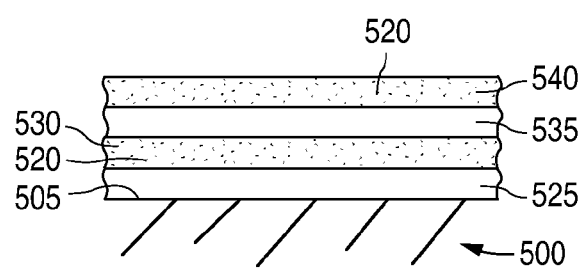

The coating may also have multiple primer and reservoir layers with the layers alternating between the two types of layers through the thickness of the coating. For instance, FIG. 11D depicts substrate 500 with a primer layer 525 deposited on surface 505, followed by reservoir layer 530 deposited on primer layer 525. A second primer layer, primer layer 535, can then be deposited on reservoir layer 530. Reservoir layer 540 is deposited over primer layer 535. Reservoir layers 530 and 540 have active agent 520 dispersed within the polymer. The different layers through the thickness of the coating can contain the same or different components. For instance, primer layers 525 and 535 can contain the same or different polymers. Furthermore, reservoir layers 530 and 540 can contain the same or different polymers or active agents.

By way of example, and not limitation, primer layer 510 in FIG. 11C can have any suitable thickness, examples of which can be in the range of about 0.1 to about 10 microns, more narrowly about 0.1 to about 2 microns. Reservoir layer 515 in FIG. 11C can have a thickness of about 0.1 microns to about 10 microns, more narrowly about 0.5 microns to about 2 microns. The amount of the active agent to be included on substrate 500 can be further increased by applying a plurality of reservoir layers 515 on top of one another.

The primer layer can be formed by applying a polymer or prepolymer to the stent by conventional methods. For example, a polymer or a prepolymer can be applied directly onto a medical device substrate in the form of a powder or by vapor deposition. In one embodiment, an unsaturated prepolymer (e.g., an unsaturated polyester or acrylates) is applied to the device, and then heat treated to cause the prepolymer to crosslink.

The polymer or prepolymer can also be applied by depositing a polymer composition onto the medical device. The polymer composition can be prepared by combining a predetermined amount of a polymer or a prepolymer and a predetermined amount of a solvent or a combination of solvents. The mixture can be prepared in ambient pressure and under anhydrous atmosphere. If necessary, a free radical or UV initiator can be added to the composition for initiating the curing or cross-linking of a prepolymer. Heating and stirring and/or mixing can be employed to effect dissolution of the polymer into the solvent. The composition can then be applied by conventional methods such as by spraying the substrate of the medical device with the composition.

The polymers used for the primer material should have a high capacity of adherence to the surface of a medical device, such as a metallic surface of a stent, or a high capacity of adherence to a polymeric surface such as the surface of a stent made of polymer, or a previously applied layer of polymeric material.

Various methods may be used to selectively heat selected regions of and to selectively apply materials on a medical device. For selectively applying materials or coatings, a controlled deposition system can be used that applies various substances only to certain targeted portions of a medical device. A representative example of such a system, and a method of using the same, is described in U.S. Pat. No. 6,395,326 to Castro et al. A controlled deposition system can be capable of depositing a substance on a medical device having a complex geometry, and otherwise apply the substance so that coating is limited to particular portions of the device. The system can have a dispenser and/or holder that support a substrate of a medical device. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir which holds a composition prior to delivery, and a nozzle having an orifice through which the composition is delivered. One exemplary type of dispenser assembly can be an assembly that includes an ink-jet printhead. Another exemplary type of a dispenser assembly can be a microinjector capable of injecting small volumes ranging from about 2 to about 70 mL, such as NanoLiter 2000 available from World Precision Instruments or Pneumatic PicoPumps PV830 with Micropipette available from Cell Technology System. Such microinjection syringes may be employed in conjunction with a microscope of suitable design.

Figure 12:
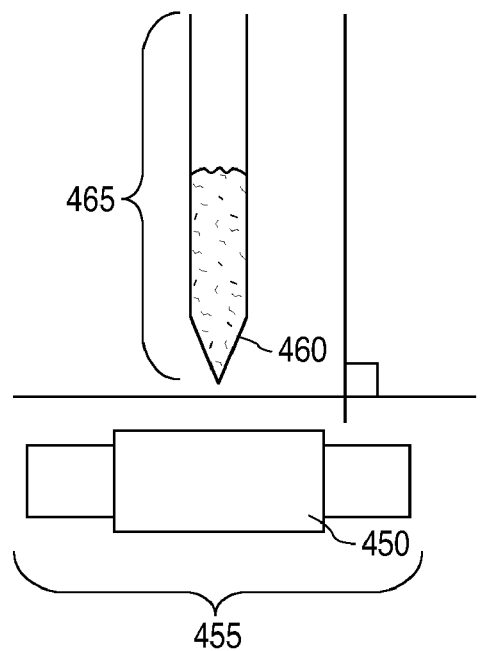
FIGS. 12-13 depict a controlled deposition system.
Figure 13:
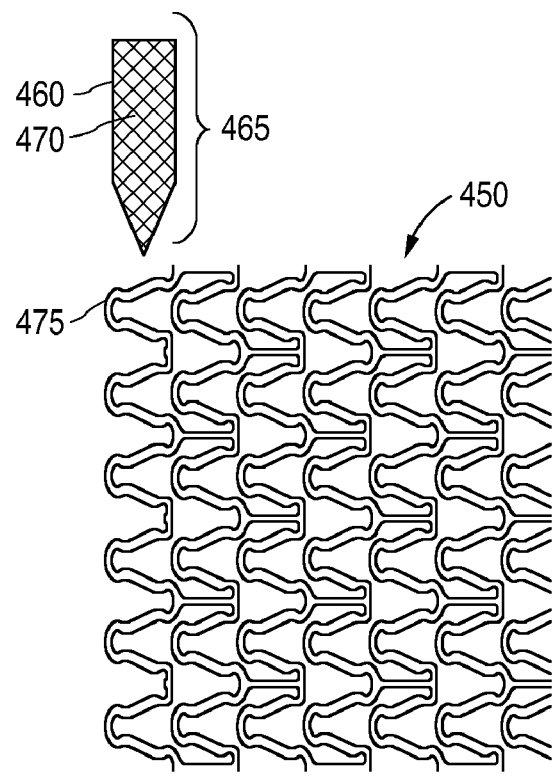

FIGS. 12 and 13 illustrate one set of embodiments of a controlled deposition system. FIG. 12 depicts a stent 450 supported by a holder assembly 455 that may be coupled to a holder motion control system and a nozzle 460 of a coating dispenser assembly 465. FIG. 11 illustrates another view of the controlled deposition system in which dispenser assembly 465 remains stationary during deposition of a coating composition 470. In this embodiment, nozzle 460 of dispenser assembly 465 is positioned at a load position over, or in contact with, a strut 475 of stent 450 as shown in FIG. 13. As composition 470 is deposited, dispenser assembly 465 remains stationary while stent 450 is moved via the holder motion control system along a predetermined path beneath the stationary nozzle 460, thereby causing composition 470 to be deposited in a preselected geometrical pattern on stent 450. In another set of embodiments, dispenser assembly 465 moves along a predetermined path while holder assembly 455 remains stationary during deposition of composition 470. In still another set of embodiments, both dispenser assembly 465 and holder assembly 455 move along respective predetermined paths during deposition of composition 470.

Additionally, in a similar manner, a controlled heating system may selectively heat selected regions of a medical device such as a stent. In one set of embodiments, the elements of the controlled deposition system described herein may be adapted for use in a controlled heating system. In one embodiment, a heating assembly with a heating apparatus such as a laser or a heated filament may be used rather than a dispenser assembly with a nozzle. The heating assembly may remain stationary while a stent is moved via a holder motion control system along a predetermined path beneath a stationary heating apparatus, thereby heating a preselected geometrical pattern on a stent. In another embodiment, the heating assembly may also be configured to move while the stent remains stationary. Additionally, both the heating assembly and the stent may be moved.

The substances of the present invention can also be selectively deposited by an electrostatic deposition process. Such a process can produce an electrically charged or ionized coating substance. The electric charge causes the coating substance to be differentially attracted to the device, thereby resulting in higher transfer efficiency. The electrically charged coating substance can be deposited onto selected regions of the device by causing different regions of the device to have different electrical potentials.

Furthermore, selective coating of an implantable medical device may be performed using photomasking techniques. Deposition and removal of a mask can be used to selectively coat surfaces of substrates. Masking deposition is known to one having ordinary skill in the art.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a stent, comprising:
   selectively heating a selected region of a scaffolding of a stent made of a polymer to modify a material property in the selected region of the scaffolding that has a variable strain profile under applied stress,
   wherein the modification accommodates the variable strain profile of the scaffolding by reducing or preventing mechanical instability when the scaffolding is under applied stress, and
   wherein the scaffolding of the stent includes a network of interconnecting struts,
   wherein the scaffolding is formed by laser cutting the network into a tube made of the polymer,
   wherein the region includes a portion of a surface of the scaffolding, and
   wherein selectively heating the selected region of the scaffolding comprises applying heat to the surface of the scaffolding, the heat being applied without dispensing material on the surface.

2. The method of claim 1, further comprising cooling the selectively heated region.

3. The method of claim 1, wherein the polymer is bioabsorbable.

4. The method of claim 1, wherein the selected region comprises a higher strain than other regions of the stent when the stent is placed under an applied stress during use.

5. The method of claim 1, wherein the selected region comprises a lower strain than other regions of the stent when the stent is placed under an applied stress during use.

6. The method of claim 1, wherein the selected region is a portion of a straight portion of a strut of the stent that experiences no or relatively no strain when the stent is placed under an applied stress, wherein the selective heating increases the modulus of the selected region.

7. The method of claim 1, wherein the selected region is a portion of a curved or bent portion of a strut of the scaffolding of the stent that bends when the stent is crimped or expanded which causes strain in the portion, wherein the selective heating decreases the modulus and increases the flexibility of the selected region.

8. The method of claim 7, wherein the portion includes abluminal, luminal, and/or side-wall surfaces of a concave part of the portion.

9. The method of claim 7, wherein the portion includes abluminal, luminal, and/or side-wall surfaces of a convex part of the portion.

10. The method of claim 7, wherein the selected region is as small as 20 microns in diameter.

11. The method of claim 7, wherein the selected region is as small as 60 microns in diameter.

12. The method of claim 7, wherein the scaffolding is completely made from a biodegradable polymer or combination of biodegradable polymers.

13. The method of claim 1, wherein the selective heating is performed with a laser and/or by conduction.

14. The method of claim 1, wherein the material property is the modulus of the polymer in the region which is increased by the selective application of heat.

15. The method of claim 1, wherein the material property is the modulus of the polymer in the region which is decreased by the selective application of heat.

16. The method of claim 1, wherein the selected region is heated to greater than or equal to the glass transition temperature of the polymer and less than or equal to the melting temperature of the polymer to increase a modulus of the selected region due to crystallization of the polymer in the selected region.

17. The method of claim 1, wherein the selected region is heated to greater than the melting temperature of the polymer and quenched to a temperature below the glass transition temperature of the polymer to decrease a modulus and increase the flexibility of the selected region.

18. The method of claim 17, wherein the polymer in the selected region is amorphous after quenching.

19. The method of claim 1, wherein the selected region is heated to greater than the melting temperature of the polymer, allowed to cool to a temperature between the glass transition temperature and the melting temperature of the polymer to allow crystallization in the selected region followed by quenching the selected region to a temperature below the glass transition temperature.

* * * * *